(12) United States Patent
Collier et al.

(10) Patent No.: US 8,269,052 B2
(45) Date of Patent: Sep. 18, 2012

(54) METHOD FOR PRODUCING PENTAFLUOROETHANE

(75) Inventors: Bertrand Collier, Saint-genis-laval (FR); Géraldine Cavallini, Saint-symphorien d'ozon (FR); Béatrice Boussand, Sainte foy les Lyon (FR)

(73) Assignee: Arkema France, Colombes (FR)

( * ) Notice: Subject to any disclaimer, the term of this patent is extended or adjusted under 35 U.S.C. 154(b) by 694 days.

(21) Appl. No.: 12/302,645

(22) PCT Filed: May 9, 2007

(86) PCT No.: PCT/FR2007/051232
§ 371 (c)(1),
(2), (4) Date: Jun. 25, 2009

(87) PCT Pub. No.: WO2007/138209
PCT Pub. Date: Dec. 6, 2007

(65) Prior Publication Data
US 2009/0326284 A1 Dec. 31, 2009

(30) Foreign Application Priority Data
May 30, 2006 (FR) ..................................... 06 04783

(51) Int. Cl.
*C07C 17/00* (2006.01)
*C07C 17/38* (2006.01)

(52) U.S. Cl. ......................................... 570/169; 570/177
(58) Field of Classification Search .................. 570/169, 570/177
See application file for complete search history.

(56) References Cited

U.S. PATENT DOCUMENTS

| 4,123,448 A | 10/1978 | Kleinpeter |
| 5,395,996 A | 3/1995 | Scott |
| 5,962,753 A * | 10/1999 | Shields et al. ................ 570/169 |

FOREIGN PATENT DOCUMENTS

| EP | 0687660 A1 | 12/1995 |
| EP | 0754170 B1 | 3/2001 |
| WO | 95/27688 A1 | 10/1995 |

* cited by examiner

*Primary Examiner* — Jafar Parsa
(74) *Attorney, Agent, or Firm* — Hunton & Williams, LLP

(57) ABSTRACT

The invention relates to a method for producing pentafluoroethane, and especially to a method comprising (i) a step during which perchloroethylene and optionally 2,2-dichloro-1,1,1-trifluoroethane and/or 2-chloro-1,1,1,2-tetrafluoroethane react(s) with hydrofluoric acid in a gaseous phase in the presence of a catalyst in an adiabatic multi-stage reactor, and optionally (ii) a step of separating the flow produced in step (i) in order to obtain a fraction of light products and a fraction of heavy products.

14 Claims, 1 Drawing Sheet

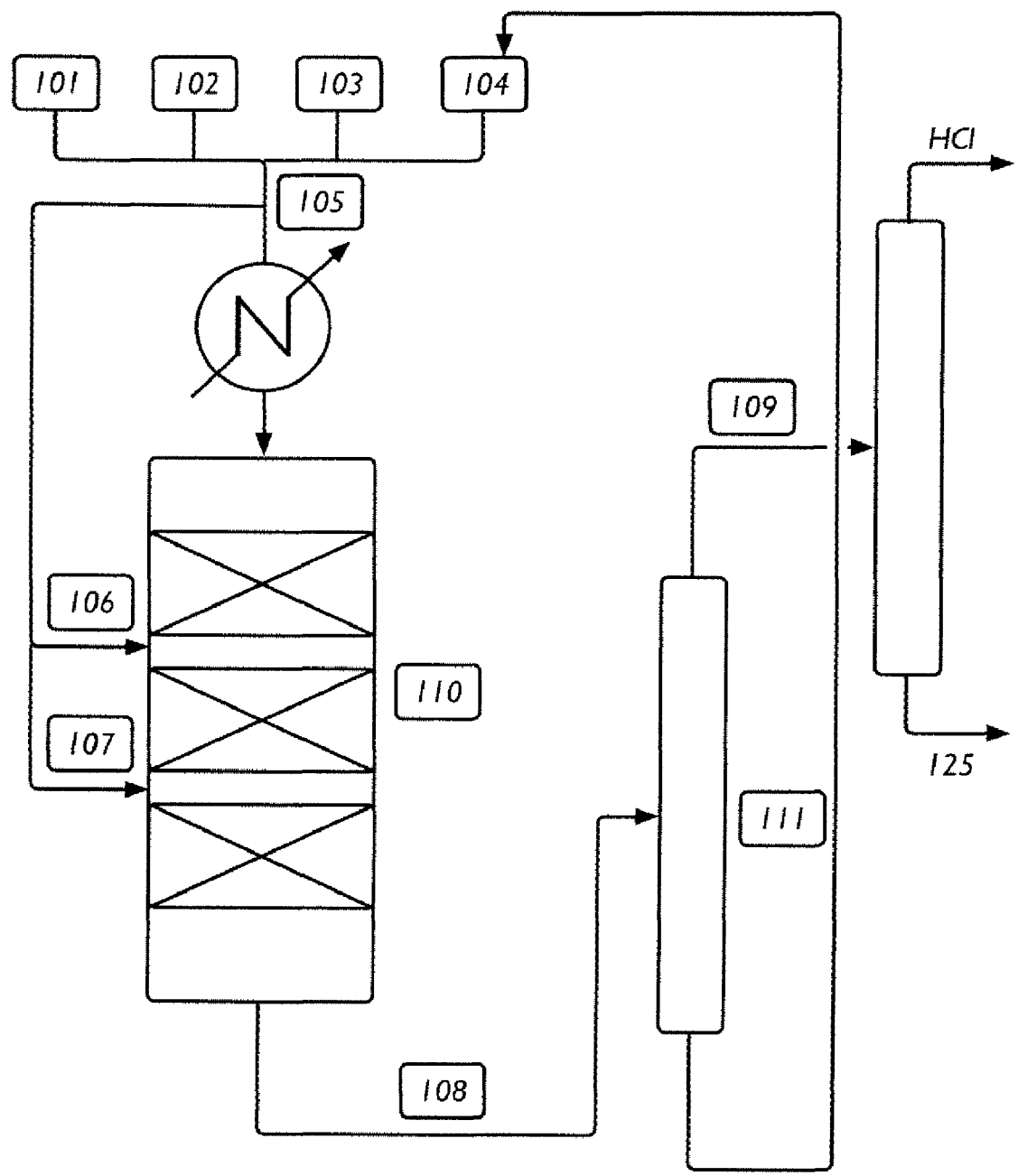

METHOD FOR PRODUCING PENTAFLUOROETHANE

CROSS-REFERENCE TO RELATED APPLICATIONS

This application is the U.S. National Phase Application of International Application No. PCT/FR2007/051232, filed May 9, 2007, which claims the benefit of French Application No. FR 0604783, filed May 30, 2006, the disclosures of each of which is hereby incorporated by reference.

FIELD OF THE INVENTION

The present invention relates to a method for producing pentafluoroethane and more particularly relates to a method for producing pentafluoroethane by reacting perchloroethylene (PER) with hydrofluoric acid (HF), in the gas phase, in the presence of a catalyst.

The reaction for fluorination of perchloroethylene with HF in the gas phase in the presence of a catalyst is known. It generally results in the formation of 2,2-dichloro-1,1,1-trifluoroethane (123), 2-chloro-1,1,1,2-tetrafluoroethane (124) and pentafluoroethane (125), with 123 as predominant product.

These compounds (denoted hereinafter, overall, by the expression "120 series") can be used either as substitutes for chlorofluorocarbons (CFCs) in the fields of foams (swelling and insulating agents) or aerosols (propellants) or in refrigeration, or as intermediates for the synthesis of these constituents. Efficient methods for the industrial production of pentafluoroethane are currently being sought.

Since the reaction for fluorination of perchloroethylene to pentafluoroethane is a strongly exothermic reaction (25-30 Kcal/mol), its use on the industrial scale poses many problems: the reaction is difficult to control, the catalyst degrades and by-products are formed in large amounts.

Document EP 687660 discloses a method for producing pentafluoroethane in which reactions are set up in two reaction zones comprising a first reaction zone in which perchloroethylene is reacted with hydrogen fluoride, in the gas phase, in the presence of a catalyst, under a pressure of between 3 bar absolute and 30 bar absolute and at a temperature of between 200° C. and 450° C., and a second reaction zone in which 2,2-dichloro-1,1,1-trifluoroethane and/or 2-chloro-1,1,1,2-tetrafluoroethane contained in the gases produced in the first reaction zone is (are) reacted with hydrogen fluoride, in the vapor phase, in the presence of a catalyst, under a pressure which does not exceed 5 bar absolute and at a temperature of between 250° C. and 500° C. said first reaction zone being maintained at a pressure above that of the second reaction zone.

Document EP 754170 describes a method for producing pentafluoroethane, which comprises (i) bringing perchloroethylene into contact with hydrogen fluoride, in the gas phase, in the presence of a first fluorination catalyst comprising chromic oxide, so as to form a stream of product comprising hydrochlorofluoroethane of formula $C_2H_1Cl_{1+x}F_{1+y}$, where x and y are each independently 0, 1, 2 or 3, it being understood that x+y is 3, and (ii) bringing the stream of product from step (i) into contact with hydrogen fluoride, in the gas phase, and in the presence of a second fluorination catalyst comprising zinc and/or nickel or a zinc and/or nickel compound deposited on chromic oxide, chromium fluoride or chromium oxyfluoride, so as to produce pentafluoroethane.

SUMMARY OF THE INVENTION

The present invention provides a method for producing pentafluoroethane from perchloroethylene which makes it possible to partly or completely solve the above-mentioned drawbacks.

BRIEF DESCRIPTION OF THE DRAWINGS

The FIGURE is a schematic view of one embodiment of the invention illustrating a three-stage adiabatic reactor and other components used in the production of pentafluoroethane.

DETAILED DESCRIPTION

The method according to the present invention is characterized in that it comprises a step during which perchloroethylene reacts with hydrofluoric acid, in the gas phase, in the presence of a catalyst in an adiabatic multistage reactor.

Preferably, the temperature at the inlet of the first stage of the adiabatic reactor is between 280 and 350° C., advantageously between 320 and 340° C. The temperature at the inlet of the subsequent stages of the adiabatic reactor may also range between 280 and 350° C., preferably between 320 and 340° C.

Within the same stage, the temperature at the inlet is in general lower than that at the outlet. Furthermore, the temperature at the inlet of the preceding stage is preferably lower than that at the inlet of the following stage.

The method according to the present invention is advantageously carried out in such a way that the temperature in the adiabatic multi-stage reactor does not exceed 410° C., preferably does not exceed 380° C.

The adiabatic reactor may comprise between 2 and 6 stages. A number of stages of between 2 and 4 is, however, preferred.

Although the fluorination step may be carried out in a wide pressure range, it is preferred to operate at an absolute pressure of between 1 and 10 bar, and advantageously between 1 and 4 bar.

The reactants are pre-vaporized before the fluorination step, and preferably vaporized and preheated to a temperature below that of the adiabatic reactor, and advantageously to a temperature of between 320 and 340° C.

The major part, preferably more than 90% by weight, of the vaporized and preheated reactants is introduced at the inlet of the first stage of the reactor. A small part, preferably less than 10% by weight, of the vaporized and preheated reactants, preferably preheated to a temperature of between 150 and 200° C., are introduced at the inter-stage level so as to have better control of the temperature of the adiabatic reactor. Preferably, the preheated reactants introduced at the inlet of the first stage of the reactor are at a temperature above that of the reactants introduced at the inter-stage level.

According to one embodiment of the invention, the stream leaving the adiabatic multi-stage reactor is subjected to a separating step in order to obtain a fraction of light products, for instance pentafluoroethane and hydrogen chloride, and a fraction of heavy products, for instance unreacted perchloroethylene, unreacted hydrofluoric acid, and the intermediate compounds, in particular 2,2-dichloro-1,1,1-trifluoroethane (123), and 2-chloro-1,1,1,2-tetrafluoroethane (124). The fraction of heavy products, after vaporization and preheating, is subsequently recycled to the reactor.

When the fraction of heavy products is recycled to the reactor, in addition to the perchloroethylene, the intermediate compounds such as 2,2-dichloro-1,1,1-trifluoroethane and 2-chloro-1,1,1,2-tetrafluoroethane also react with hydrofluoric acid.

The method may be carried out continuously or batchwise, but it is preferred to carry it out continuously.

The HF/organic reactants molar ratio is in general between 5 and 50, preferably between 10 and 30, and advantageously between 10 and 20.

The contact time, calculated as being the time taken for the gases to pass (under the reaction conditions) through the volume of catalyst, is preferably between 5 and 40 s, advantageously between 10 and 20 s.

When the pressure of the fluorination step is less than 4 bar absolute, it is often advantageous to compress the reaction products before subjecting them to the separating step. This compression may be carried out using a compressor, and makes it possible to perform the separation, when it is, for example, a distillation, under favorable energy conditions. In addition, it makes it possible to recover more than 99% of the unreacted hydrofluoric acid.

Any fluorination catalyst may be suitable for the method of the present invention. The catalyst used preferably comprises the oxides, halides, oxyhalides or mineral salts of chromium, of aluminum, of cobalt, of manganese, of nickel, of iron or of zinc, and may be supported. By way of example, mention may be made of alumina, aluminum fluoride or aluminum oxyfluoride.

A chromium oxide ($Cr_2O_3$)-based catalyst, optionally including another metal in an oxidation state above zero and selected from Ni, Co, Mn and Zn, is preferably used. Advantageously, this catalyst may be supported on alumina, fluorinated aluminum or aluminum oxyfluoride.

A mixed catalyst composed of nickel oxides, halides and/or oxyhalide and of chromium oxides, halides and/or oxyhalide, deposited on a support consisting of aluminum fluoride or of a mixture of aluminum fluorides and alumina, is most particularly suitable for the method of the present invention.

This catalyst may be prepared in a manner known per se, from activated alumina. The latter may, in a first step, be converted to aluminum fluoride or to a mixture of aluminum fluoride and alumina, by fluorination using hydrofluoric acid, optionally in the presence of air or of an inert gas such as nitrogen, at a temperature in general of between 200 and 450° C., preferably between 250 and 400° C. The support is subsequently impregnated with aqueous solutions of chromium salts and nickel salts or with aqueous solutions of chromic acid, of nickel salt and of a chromium-reducing agent such as methanol.

When chromic acid ($CrO_3$) is used as chromium precursor, this chromium can be reduced by any means known to those skilled in the art, provided that the technique used is not harmful to the properties of the catalyst and therefore to the activity thereof. The preferred reducing agent is methanol.

As chromium and nickel salts, use is preferably made of chlorides, but it is also possible to use other salts, such as, for example, oxalates, formates, acetates, nitrates and sulfates, or nickel dichromate, provided that these salts are soluble in the amount of water likely to be absorbed by the support.

The mixed catalyst used in the method according to the invention may also be prepared by direct impregnation of alumina with solutions of the chromium and nickel compounds mentioned above. In this case, the conversion of at least a part of the alumina to aluminum fluoride is carried out during the catalyst-activation step.

The activated aluminas to be used for the preparation of the mixed catalyst are well-known products that are commercially available. They are generally prepared by calcining alumina hydrates at a temperature of between 300 and 800° C. The activated aluminas that can be used in the context of the present invention may contain large contents (up to 100 ppm) of sodium, without this harming the catalytic activity.

The mixed catalyst may contain, by mass, from 0.5% to 20% of chromium and from 0.5% to 20% of nickel, and preferably between 2% and 10% of each of the metals in a nickel/chromium atomic ratio of between 0.5 and 5, preferably in the region of 1.

Before use in the perchloroethylene fluorination reaction, the catalytic solid is subjected beforehand to an activation process.

This treatment, carried out "in situ" (in the fluorination reactor) or in an appropriate apparatus, generally comprises the following steps:

drying at low temperature in the presence of air or of nitrogen, drying at high temperature (250 to 450° C., preferably 300 to 350° C.) under nitrogen or under air, fluorination at low temperature (180 to 350° C.) by means of a mixture of hydrofluoric acid and nitrogen, with the HF content being controlled in such a way that the temperature does not exceed 350° C., and finishing under a stream of pure hydrofluoric acid or hydrofluoric acid diluted with nitrogen, at a temperature that may range up to 450° C.

Although not necessary for the fluorination reaction, it may be judicial to introduce, with the reactants, oxygen in a low amount. This amount may, according to the operating conditions, range from 0.02 mol % to 1 mol % relative to the reactants that go into the reactor. The oxygen may be introduced into the reactor either in a pure state or diluted in an inert gas such as nitrogen. The oxygen may also be introduced in the form of air. The introduction of oxygen, whatever the form adopted, may be carried out continuously or sequentially.

The adiabatic reactor may be made from materials resistant to corrosive media comprising hydrofluoric acid, for example Hastelloy and Inconel.

The method according to the present invention makes it possible to have good control of the exothermicity of the reaction and therefore to partly or completely avoid the drawbacks such as premature deactivation of the catalyst. In addition, the method makes it possible to obtain a very high pentafluoroethane productivity. Furthermore, this method makes it possible to recycle the unreacted reactants and the intermediate compounds without prior purification.

One embodiment of the invention is described with reference to the FIGURE. An adiabatic reactor (110), consisting of three stages and containing a pre-activated, optionally supported, chromium oxide-based catalyst, is fed with a gas stream (105) comprising, on the one hand, perchloroethylene (101), hydrofluoric acid (102) and, optionally, air (103) and, on the other hand, HF, PER and intermediate compounds (predominantly 2,2-dichloro-1,1,1-trifluoroethane and 2-chloro-1,1,1,2-tetrafluoroethane) recycled from the stream (104). The gas stream (105) is preheated to 300° C. before being introduced into the reactor and the temperature at the inlet of the first stage is maintained between 320 and 340° C. The second stage of the reactor is fed with the gas stream from the first stage and, optionally, with the gas stream (106) comprising the reactants preheated to 180° C. and, optionally, air. The temperature at the inlet of the second stage is also maintained between 320 and 340° C. The third stage of the reactor is fed with the gas stream derived from the second stage, and optionally, with the gas stream (107) comprising the reactants preheated to 180° C. and, optionally, air. The temperature at the inlet of the third stage is also maintained between 320 and 340° C. The gas stream (108) leaving the reactor is sent to the distillation column (111), so as to give, at the top, a fraction of light products (109) comprising in particular pentafluoroethane and HCl, and at the bottom, a fraction of heavy products comprising HF, PER and intermediate compounds (predominantly 2,2-dichloro-1,1,1-trifluoroethane and 2-chloro-1,1,1,2-tetrafluoroaethane). The fraction of heavy products leaves the distillation column via the bottom and is subsequently recycled to the reactor, while the fraction of light products is subjected to a distillation step (112) so as to separate the HCl from the pentafluoroethane. The pentafluoroethane is subsequently purified.

Throughout the duration of the reaction, the temperature of the multi-stage reactor is maintained at no higher than 380° C., and the absolute pressure is approximately 3 bar.

The invention claimed is:

1. A method of producing pentafluoroethane comprising the step of:
   (i) reacting an organic reactant comprising perchloroethylene with hydrofluoric acid, in the gas phase, in the presence of a catalyst, in a single adiabatic multi-stage reactor, to produce a product comprising pentafluoroethane, and
   (ii) optionally separating said product into a fraction of light products and a fraction of heavy products;
   wherein said adiabatic multi-stage reactor comprises a first stage comprising an inlet, and the temperature at said inlet ranges from about 280° C. to about 350° C.

2. The method of claim 1, wherein said organic reactant further comprises 2,2-dichloro-1,1,1-trifluoroethane and/or 2-chloro-1,1,1,2-tetrafluoroethane.

3. The method of claim 1, wherein the temperature at said inlet ranges from about 320° C. to about 340° C.

4. The method of claim 1, wherein the temperature in said adiabatic multi-stage reactor does not exceed 410° C.

5. The method of claim 4, wherein the temperature in said adiabatic multi-stage reactor does not exceed 380° C.

6. The method of claim 1, wherein step (i) occurs at a pressure ranging from 1 to 10 bar absolute.

7. The method of claim 6, wherein step (i) occurs at a pressure ranging from 1 to 4 bar absolute.

8. The method of claim 2, further comprising separating said product into a fraction of light products and a fraction of heavy products and recycling said fraction of heavy products to the adiabatic multi-stage reactor.

9. The method of claim 1, wherein the molar ratio of said hydrofluoric acid to said organic reactant ranges from 5 to 50.

10. The method of claim 1, wherein the molar ratio of said hydrofluoric acid to said at least one organic reactant ranges from 10 to 30.

11. The method of claim 1, wherein the molar ratio of said hydrofluoric acid to said at least one organic reactant ranges from 10 to 20.

12. The method of claim 1, wherein said catalyst is a chromium oxide ($Cr_2O_3$)-based catalyst.

13. The method of claim 12, wherein said catalyst additionally comprises a metal in an oxidation state above zero.

14. The method of claim 13, wherein said metal comprises Ni, Co, Mn, Zn, or mixtures thereof.

\* \* \* \* \*